United States Patent
Engel et al.

(12)

(10) Patent No.: US 6,313,306 B1
(45) Date of Patent: Nov. 6, 2001

(54) N-(2-MERCAPTOETHYL)-1,3-THIAZOLIDINES AND THEIR USE AS ODORANTS AND FLAVORINGS

(75) Inventors: Wolfgang Engel, Neufahrn; Peter Schieberle, Freising, both of (DE); Matthias Güntert, Teterboro, NJ (US); Stefan Lambrecht, Holzminden (DE)

(73) Assignee: Haarmann & Reimer GmbH, Holzminden (DE)

( * ) Notice: Subject to any disclaimer, the term of this patent is extended or adjusted under 35 U.S.C. 154(b) by 34 days.

(21) Appl. No.: 09/610,757

(22) Filed: Jul. 6, 2000

(30) Foreign Application Priority Data

Jul. 12, 1999  (DE) ............................... 199 32 495

(51) Int. Cl.[7] ....................... C07D 277/04; C07D 277/06
(52) U.S. Cl. ............................................. 548/146
(58) Field of Search ............................... 548/146

(56) References Cited

U.S. PATENT DOCUMENTS 3,980,089   9/1976   Pittet et al. ........................ 131/144

FOREIGN PATENT DOCUMENTS 1428902   12/1966   (FR) .

OTHER PUBLICATIONS

Food. Rev. Int., 13(4), month unavailable, 1997, pp. 553–575, Josef Kerler et al, "α–Acetyl–N–Heterocycles in the Maillard Reaction".

Chemical Abstracts, vol. 104, No. 13, Mar. 31, 1986, Columbus, Ohio, US; abstract No. 109619a, Seite 726; XP002149361, Zusammenfassung, & JP 60 149592 A (Hasegawa, T., Co., Ltd.) Aug. 7, 1985.

Tank, CA 55:796i, Jan. 9, 1961.*

* cited by examiner

*Primary Examiner*—Laura L. Stockton
(74) *Attorney, Agent, or Firm*—Joseph C. Gil; Noland J. Cheung

(57) ABSTRACT

Substituted N-Mercaptoethyl-1,3-thiazolidines are novel compounds which can be used in odorants and flavorings.

2 Claims, No Drawings

N-(2-MERCAPTOETHYL)-1,3-THIAZOLIDINES AND THEIR USE AS ODORANTS AND FLAVORINGS

FIELD OF THE INVENTION

The invention relates to N-(2-Mercaptoethyl)-1,3-thiazolidines, processes for their preparation and their use as aromatizing substance in foods and drinks and for spraying food aromas and for room air fragrancing.

BACKGROUND OF THE INVENTION

In the flavor industry, there is still a great demand for substances which impart an of-factory impression to foods and drinks such as results in the thermal treatment during boiling, baking, and roasting of foods. The resultant aromatizing compounds exhibit especially roasted notes. However, these compounds in particular have been scarcely alable. In addition to the flavor, which is larely actually perceived retronasally as an odor, the orthonasally perceived odor currently plays an important role. Therefore, flavor compounds are also of importance which impart a correspondingly strong and typical odor to a food or drink.

The most important reaction which proceeds in the thermal treatment of foods is the reaction between reducing, sugars and amino acids which is called the Maillard reaction. During this Maillard reaction, flavorings of the heterocycle class of chemical substances are formed. These compounds contain one or more heteroatoms, various side chains and are aromatic or partially hydrogenated (P. A. Finot, H. U. Aeschbacher, R. F. Hurrell, R. Liardon, The Maillard Reaction in Food Processing, Human Nutrition and Physiology, Birkhäuser Verlag, Basle, 1990).

SUMMARY OF THE INVENTION

As a novel class of odorant and flavoring substances, N-(2-Mercaptoethyl)-1,3-thiazolidines and their disulphides of the formula

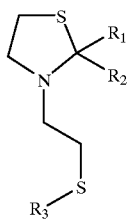

have been found, wherein $R_1$, $R_2$ and $R_3$ are identical or different and $R_1$ is hydrogen, methyl, ethyl, propyl or isopropyl, $R_2$ is hydrogen, acetyl, propionyl, isobutyryl, methyl, ethyl, propyl or isopropyl and $R_3$ is hydrogen or

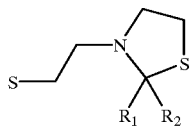

Substituted N-Mercapoethyl-1,3-thiazolidines and their disulphides are odorants and flavorings.

DETAILED DESCRIPTION OF THE INVENTION

The inventive substituted N-Mercaptoethyl-1,3-thiazolidines and their disulphides, in particular N-(2-Mercaptoethyl)-1,3-thiazolidine, surprisingly have very low threshold values. For example, the inventive N-(2-Mercaptoethyl)-1,3-thiazolidine has a surprisingly low threshold value at 0.005 ng/l in air. This makes it possible to use it as an aromatizing constituent at very low concentrations. In addition, N-(2-Mercaptoethyl)-1,3-thiazolidine imparts a particularly strong and typically roasted flavor to foods.

Compared with the thiazolines, among which, especially 2-acetyl-2-thiazoline is a known flavoring (J. Kerler, J. G. M. van der Veen, H. Weenan, Food Rev. Int., 1997, 13, 553–575), little is known to date on the thiazolidine class of substances as flavorings. Although in the scientific literature, thiazolidines are also described as reaction products of sugars and amino acids, these thiazolidines are not, however, distinguished by corresponding aromatizing properties and therefore do not appear either as industrially used flavorings.

Surprisingly, N-(2-Mercaptoethyl)-1,3-thiazolidine develops virtually no retronasal flavor activity in aqueous solutions, that is to say, on tasting, it is scarcely perceived to have flavor. However, it has a very strong orthonasal action and develops an intensive roasted odor note. Thus, although the flavoring N-(2-Mercaptoethyl)-1,3-thiazolidine of the present invention has similar sensory properties to furfurylthiol, it has a much more intense aroma and has a considerably lower odor threshold. This was determined at 0.005 ng/l in air. Thus, the compound belongs to the most aroma-intensive compounds, which are known in flavor chemistry.

N-(2-Mercaptoethyl)-1,3-thiazolidine was identified as a thermal reaction product of cysteamine with fructose (Example 1). Its structural origin, however, is not as simple to explain. Presumably, cysteamine and formaldehyde contribute to its thermal formation. It was identified by fractionating the extract from the reaction mixture by gas chromatography and subsequent mass spectrometric analysis. N-(2-Mercaptoethyl)-1,3-thiazolidine was unambiguously identified by comparison with the analytical data of an authentic sample.

In addition, systematic experiments have also been carried out by using a chromatograpic method which is termed gas chromatography-olfactometry (GC-O). In this method, the compounds which were separated during the chromatographic process are sniffed individually with the nose at the end of the capillary column. Using these methods, the olfactory and gustatory qualities of N-(2-Mercaptoethyl)-1,3-thiazolidine were pre-evaluated.

The structure was demonstrated by comparison with synthesized N-(2-Mercaptoethyl)-1,3-thiazolidine. N-(2-Mercaptoethyl)-1,3-thiazolidine can be prepared starting from thiazolidine. Thiazolidine is admixed with ethylene sulphide and heated under an inert gas atmosphere for 24 hours at 80° C. After purification N-(2-Mercaptoethyl)-1,3-thiazolidine is obtained (Example 2).

The compound of the present invention N-(2-Mercaptoethyl)-1,3-thiazolidine is, because of its outstanding organoleptic character, particularly suitable as a flavoring for use in flavor compositions. It is particularly surprising that N-(2-Mercaptoethyl)-1,3-thiazolidine imparts a very intensive roasted note to the relevant compositions at extremely low concentrations. In this case the flavor is perceived particularly by smell (orthonasally).

In ready-to-use flavors, the amount of the compound of the present invention used is preferably between 0.00005 and 1% by weight, in particular between 0.0001 and 0.5% by weight, based on the total composition. Flavor compositions of this type can be used in the entire food and drink sector. In particular, they are suitable for aromatizing snacks, soups, sauces, ready-to-eat meals, fat compositions, bakery products, yogurt, ice cream and confectionery products. The dosage of flavor compositions of this type is preferably 0.005 to 2% by weight, in particular between 0.01 and 1% by weight, based on the finished food or drink.

The ready-to-use flavors can be used in liquid form or in spray-dried form or in encapsulated formn. Whereas, in liquid form, they are used in a solvent which is customary in practice, such as ethanol, propylene glycol, vegetable oil triglycerides or triacetin, the dry flavors are produced by spray-drying or by encapsulation according to a process customary in the flavor industry. These are the extrusion and spray granulation processes.

Owing to the intense odor activity, the compound of the present invention N-(2-Mercaptoethyl)-1,3-thiazolidine is also suitable, in particular, for aromatizing packages of foods and drinks, and also for other applications (e.g. spraying of food aromas and for room air fragrancing).

The invention is further illustrated but is not intended to be limited by the following examples in which all parts and percentages are by weight unless otherwise specified.

EXAMPLES

Example 1
Reaction Between Cysteamine and Fructose 3.3 mmol of cysteamine and 10 mmol of fructose are heated to 145° C. in 20 minutes in a phosphate buffer at pH 7. The flavorings are obtained by extraction with ethyl ether and subsequent concentration. They were identified by GC/MS.

Example 2
Preparation of 2-substituted N-(2-Mercaptoethyl)-1,3-thiazolidines a) Preparation of 2-substituted thiazolidines 1.1 mmol of carbonyl compound or dicarbonyl compound are reacted with 1.1 mmol of cysteamine hydrochloride in oxygen-free aqueous phosphate buffer solution (pH=7) under a protective gas atmosphere. The reaction is carried out, in the case of the reactive components formaldehyde, acetaldehyde and methylglyoxal, at 0° C. The reaction is followed by gas chromatography. After work-up and chromatographic purification, the corresponding thiazolidines are obtained.

b) Preparation of the 2-substituted N-(2-Mercaptoethyl)-1,3-thiazolidines 10 mmol of 2-substituted thiazolidine are admixed in a glass autoclave with 10 mmol of ethylene sulphide and heated without solvent at 80° C. for 24 hours under a protective gas. The reaction mixture is taken up in sodium hydroxide solution and washed with dichloromethane. The aqueous phase is adjusted to pH 8 with hydrochloric acid and extracted with dichloromethane. The N-(2-Mercaptoethyl)-thiazolidines are obtained at a purity of approximately 90–96% and in a yield of 75–88%.

Mass spectrum of N-(2-Mercaptoethyl)-thiazolidine

| m/z | Intensity % |
|---|---|
| 27 | 12 |
| 28 | 12 |
| 42 | 45 |
| 45 | 12 |
| 56 | 12 |
| 57 | 13 |
| 59 | 9 |

-continued

| m/z | Intensity % |
|---|---|
| 61 | 15 |
| 88 | 7 |
| 102 | 100 |

Example 3
Preparation of a Roasted Flavor

The following were mixed (all quantities in g):

| | |
|---|---|
| 3-Methylthiopropanal (1% in vegetable oil triglycerides) | 1.0 |
| 2,3-Diethyl-5-methylpyrazine | 1.0 |
| Isoamyl caprylate | 1.0 |
| Diacetyl (10% in triacetin) | 2.0 |
| 2-Methylbutyric acid | 5.0 |
| Isoamyl alcohol | 10.0 |
| Delta-dodecalactone | 10.0 |
| 2-Phenylethanol | 15.0 |
| 2-Methylbutanal | 20.0 |
| Caprylic acid (10% in triacetin) | 25.0 |
| Dimethyloxyfurone (1% in propylene glycol) | 100.0 |
| 2,5-Dimethyl-4-hydroxy-3(2H)-furanone (15% in propylene glycol) | 500.0 |
| Vegetable oil triglycerides | 9310.0 |
| Total | 10000.0 |

When 0.1–0.5 g of the solvent vegetable oil triglycerides were replaced by 0.1–0.5 g of N-(2-Mercaptoethyl)-thiazolidine, the flavor became markedly more typical in the direction towards roasted bread crust.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Compounds of the formula

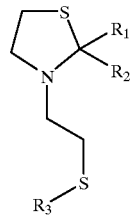

wherein $R_1$, $R_2$ and $R_3$ are identical or different and $R_1$ is hydrogen, methyl, ethyl, propyl, or isopropyl; $R_2$ is hydrogen, acetyl, proplonyl, isobutyryl, methyl, ethyl, propyl, or isopropyl and $R_3$ is hydrogen or

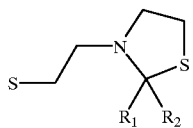

provided that $R_1$ and $R_2$ are not methyl when $R_3$ is hydrogen.

2. A compound according to claim 1, wherein said compound is N-(2-Mercaptoethyl)-1,3-thiazolidine.

* * * * *